(12) United States Patent
Levin

(10) Patent No.: US 6,861,954 B2
(45) Date of Patent: Mar. 1, 2005

(54) TRACKING MEDICAL PRODUCTS WITH INTEGRATED CIRCUITS

(75) Inventor: Bruce H. Levin, 125 Broome La., Marion Station, PA (US) 19066

(73) Assignee: Bruce H. Levin, Marion Station, PA (US)

(*) Notice: Subject to any disclaimer, the term of this patent is extended or adjusted under 35 U.S.C. 154(b) by 280 days.

(21) Appl. No.: 10/106,183

(22) Filed: Mar. 27, 2002

(65) Prior Publication Data

US 2002/0143320 A1 Oct. 3, 2002

Related U.S. Application Data

(63) Continuation-in-part of application No. 09/883,991, filed on Jun. 20, 2001.
(60) Provisional application No. 60/280,206, filed on Mar. 30, 2001.

(51) Int. Cl.[7] .................................................. G08B 13/14
(52) U.S. Cl. ........................ 340/572.1; 340/539.12; 606/1
(58) Field of Search .......................... 340/573.4, 573.1, 340/572.1, 539.12, 539.13; 604/362; 606/1

(56) References Cited

U.S. PATENT DOCUMENTS

| | | | | |
|---|---|---|---|---|
| 5,673,037 A | * | 9/1997 | Cesar et al. ............. | 340/10.32 |
| 5,729,697 A | * | 3/1998 | Schkolnick et al. ........... | 705/23 |
| 5,777,561 A | * | 7/1998 | Chieu et al. .............. | 340/10.32 |
| 5,942,987 A | * | 8/1999 | Heinrich et al. .......... | 340/10.42 |
| 5,949,335 A | * | 9/1999 | Maynard .................. | 340/572.1 |
| 5,950,632 A | * | 9/1999 | Reber et al. ................ | 128/898 |
| 6,195,005 B1 | * | 2/2001 | Maloney .................. | 340/568.1 |
| 6,232,870 B1 | * | 5/2001 | Garber et al. .............. | 340/10.1 |
| 6,366,206 B1 | * | 4/2002 | Ishikawa et al. .......... | 340/573.1 |
| 6,535,129 B1 | * | 3/2003 | Petrick ..................... | 340/572.1 |
| 2002/0067263 A1 | * | 6/2002 | Tafoya et al. ............. | 340/572.1 |
| 2002/0116274 A1 | * | 8/2002 | Hind et al. ................... | 705/23 |
| 2002/0119770 A1 | * | 8/2002 | Twitchell, Jr. .............. | 455/422 |
| 2003/0016122 A1 | * | 1/2003 | Petrick ..................... | 340/10.41 |
| 2003/0032446 A1 | * | 2/2003 | Pincus ........................ | 455/556 |
| 2003/0052788 A1 | * | 3/2003 | Kwong-Tai Chung ... | 340/573.1 |
| 2003/0127508 A1 | * | 7/2003 | Jones .......................... | 235/375 |
| 2003/0164401 A1 | * | 9/2003 | Andreasson et al. ........ | 235/385 |

* cited by examiner

Primary Examiner—Thomas Mullen
(74) Attorney, Agent, or Firm—Kenyon & Kenyon (57) ABSTRACT

A system and method of tracking medical products provides for associating a group of medical products with a group location based on a group radio frequency identification (RF ID) device signal, where the group includes a first unit and a second unit. The first unit is associated with a first remote location based on a first unit RF ID device signal. The method further provides for associating the second unit with a second remote location based on a second remote location based on a second unit RF ID device signal. The signals uniquely identify the units and the group.

27 Claims, 9 Drawing Sheets

| 170 | SURGICAL IMPLEMENT IDENTIFIER 172 | TIME OF INITIAL REGISTRATION 174 | CHECK OUT TIME 176 | CHECK IN TIME 178 | CHECK IN LOCATION 180 | TYPE OF SURGICAL IMPLEMENT 182 |
|---|---|---|---|---|---|---|
| 184 | 12 | 12:00 | 12:07 | 14:23 | GARBAGE | SPONGE |
| 186 | 13 | 12:01 | 12:12 | 13:01 | MAIN TABLE | SPONGE |
| 188 | 14 | 12:01 | 12:13 | 15:07 | GARBAGE | SCALPEL |
| 190 | --- | --- | --- | --- | --- | --- |

TRACKING MEDICAL PRODUCTS WITH INTEGRATED CIRCUITS

This application is a continuation-in-part of application Ser. No. 09/883,991 filed Jun. 20, 2001, and claims the benefit of provisional application No. 60/280,206 filed Mar. 30, 2001.

FIELD OF THE INVENTION

The present invention relates to devices, labels, methods, and systems to monitor and track medical implements and products containing integrated circuits. Specifically, embodiments of the present invention relate to preventing these medical implements from being inadvertently left within a human or animal following completion of medical procedures. In addition, embodiments of the present invention are meant to decrease errors resulting from sub-optimal production, processing, distribution, and administration of medical products, including but not limited to pharmaceuticals and blood products. Embodiments of the present invention also pertain to managing medical products, medical devices and disposables, such as medications, blood, and tissue products, and more particularly to the use of electronic means such as radio frequency identification (RF ID) devices to assist in the management process from point of origin to end use.

BACKGROUND OF THE INVENTION

During surgery it is necessary to place surgical implements, such as sponges, scalpels, needles, gauzes, and the like near or into a wound cavity. Even though thorough manual counts are conducted following the completion of surgery, this method is time consuming, tedious and error prone. Indeed, surgical implements are too frequently left inside patients resulting in complications including trauma, pain, infection or death.

A number of conventional methods exist to make sure that all surgical implements have been removed from a patient, but all have drawbacks. The most well known method is to use X-rays. In this procedure, the surgical implements have radio opaque material embedded within them. Following the completion of surgery and suturing of the patient, an X-ray machine is moved over the patient and an X-ray is taken of the wound area to determine whether radio opaque materials are present in the patient. However, some materials may be too small to be easily seen on X-ray, or they may be otherwise obscured by bone or tissues within radio dense areas. If any surgical implements are found on the X-ray within the sutured area, then the patient is reopened to retrieve the retained materials. This way, implements left within a patient are removed. However, each time this procedure is performed, expensive operating room time is wasted and other patients may have their surgeries delayed. Furthermore, the patient is subjected to more anesthesia time and otherwise unnecessary radiation.

Another method suggested by U.S. Pat. No. 4,193,405 to Abels, detects a radio-frequency ("RF") transponder embedded in a surgical sponge. In this method, tagging of surgical articles with ferrite or other semiconductor material is done such that when they are exposed to two selected frequencies the material will resonate. This resonance can then be detected by a RF receiver. However, this method merely relates to a transponder, no data is recorded as to type of object, time rank of object, nor does it allow for master categorization which would alert the user that an object is in fact missing, even in the absence of a detected failure. Hence, this level of safety is easily breached.

In U.S. Pat. No. 4,658,818 to Miller, a miniature battery-powered oscillator is attached to each surgical implement and activated prior to its initial use. The output of each oscillator is in the form of a low powered pulse which is coupled to the body's fluids and tissue. After the surgery is completed, but prior to suturing, a detection system is used to sense for any pulses generated within the body. However, this system also does not provide information as to object type, rank timing or master categorization, and merely serves as a pulse alarm.

Another system that has recently been devised is disclosed in U.S. Pat. No. 5,931,824 to Stewart. This system is drawn to placing machine-readable information on individual surgical sponges. In addition, each sponge has X-ray detectable material embedded within it. This system requires that each sponge is scanned which is tedious, and allows for neither non-orientational registration nor perimeter scanning.

Additionally, sub-optimal logistics result in medication and other errors, which have resulted in significant morbidity and mortality.

Furthermore, tracking and distributing medications and blood or tissue products from their points of origin to their appropriate administration to patients requires a very major commitment of dedicated resources to maintain acceptable safety and efficiency. Unfortunately, commonly utilized methodologies can be expensive, wasteful, and potentially hazardous as they rely heavily on human input and require sustainable levels of efficiency that may be unrealistically high. As any breach of vigilance resulting from suboptimal visual or other input, stress, fatigue, repetition or distraction can have dire consequences at multiple points, risk exposure is significant. Medications may be poorly tracked leading to shortages in inventory or inappropriate use of outdated medications. Inappropriate formulations or concentrations of drug may be found in improper locations in the hospital, clinic or other patient care facility and this can result in improper dosing.

Furthermore, allergies or other adverse medication reactions, as well as hazardous drug interactions may go unrecognized or ineffectively addressed by patient care providers or other ancillary medical staff. Blood product preparation is an expensive and complex endeavor and current procedures for tracking blood products at the point of collection through the point of distribution can be sub-optimal. Additionally, the procedures can be subject to hazard as human error at several points can lead to fatalities. For example, one concern is the potential for busy clinicians to misread one or more of a series of numbers and letters on a patient ID bracelet or unit of packed red blood cells during a severe bleeding episode in an operating room. Hence, there is a need for effective and safe methodologies for tracking medications and blood and other tissue products from the point of production to the point of administration.

A number of tracking devices have been well documented. For example, U.S. Pat. No. 6,130,613 shows a radio frequency identification stamp (10) having a substrate (24) with a first surface (12) and a second surface (18). The first surface (12) is printed with indicia indicating at least a postage value. An antenna (16) is formed on the second surface (18) and a radio frequency identification circuit chip (20) is secured to the second surface (18) and coupled to the antenna (16). A layer (22) of adhesive is also disposed on the second surface (18). A mailing label (600) includes indicia (614) printed on a first surface, and an antenna (616) coupled to a radio frequency identification circuit chip (620) on a second surface (618). A layer (622) of adhesive covers the second surface. The layer bonds the circuit chip (620) to the second surface and couples the circuit chip (620) to the antenna (616). The circuit chip (620) may retain a tracking number, and more preferably, retains sender information (601), recipient information (602), service type information (603) and billing instructions (604).

SUMMARY OF THE INVENTION

The present invention provides devices, methods, and systems that monitor and track medical materials, including surgical implements.

In an embodiment of the present invention, a surgical implement including at least one integrated circuit that uniquely identifies the surgical implement by a unique identifier is provided.

In another embodiment of the present invention, a method for monitoring and tracking surgical implements is provided. The method includes identifying at least one surgical implement including an integrated chip, where each surgical implement is uniquely identified. Another method of the present invention provides for monitoring and tracking medical materials. This method includes uniquely identifying at least one medical material by a unique identifier, each medical material including at least one integrated circuit having the unique identifier programmed therein and monitoring each medical material by its unique identifier. In another embodiment of the present invention, a method for monitoring surgical implements in conjunction with a surgical procedure is provided. The method includes initializing at least one surgical implement where each surgical implement includes an integrated circuit, registering the surgical implement prior to a surgical procedure by programming a unique identifier in the integrated circuit, and accounting for the surgical implement at the completion of the surgical procedure by receiving the unique identifier from the surgical instrument.

The present invention also includes systems. In one embodiment of the present invention a system for monitoring and tracking surgical implements is provided. The system includes at least one surgical implement, each surgical implement including an integrated circuit that stores a unique identifier of the surgical instrument and a detector that detects the surgical implement by detecting the unique identifier from the integrated circuit. Another embodiment of the present invention includes a system for monitoring and tracking surgical implements including at least one surgical implements, including at least one integrated circuit and a sensor for sensing the surgical implements based on a signal received from each integrated circuit. In another embodiment of the present invention, a system for monitoring surgical implements used in conjunction with a surgical procedure is provided. This system includes at least one surgical implement comprising an integrated circuit, the integrated circuit associating a unique identifier with each of the surgical implements and emitting a signal containing the unique identifier, a detector that detects the signal emitted by the surgical implement, and an output device to process information provided by the detector. The present invention also provides another embodiment of a system, including at least one surgical implement comprising an integrated circuit, the integrated circuit associating a unique identifier with each of the surgical implements and emitting a signal containing the unique identifier, a platform with a detector that detects the signal and determines a placement and removal of each of the surgical implements from the platform based on the detected signal, and an output device that receives and processes information provided by the detector. Another embodiment of the present invention provides a system for monitoring patients including at least one medical material, each medical material including a first integrated circuit, at least one patient identification tag, each patient identification tag including a second integrated circuit, and a sensor that monitors the medical materials and patient identification tags based on signals received from the first and second integrated circuits.

The present invention also provides a medical label including at least one integrated circuit, where the integrated circuit uniquely identifies a medical product the medical label is attached to. In another embodiment of the present invention, a blood product label is provided, which includes a label attached to a blood product, the label including at least one integrated circuit that uniquely identifies the blood product. The present invention also provides a blood product container including the blood product label. Finally, the present invention provides medical product including at least one integrated circuit that uniquely identifies the medical product by a unique identifier.

DETAILED DESCRIPTION

Embodiments of the present invention relate to methods, devices, labels, and systems for monitoring medical implements products containing integrated circuits, microchips, or Radio Frequency Ids (RFID). Prior to a medical procedure, each of the implements to be used is registered with a sensor system such that the implement is uniquely identified. Following the medical procedure, each of the implements that was registered is then accounted for.

Figure 1:
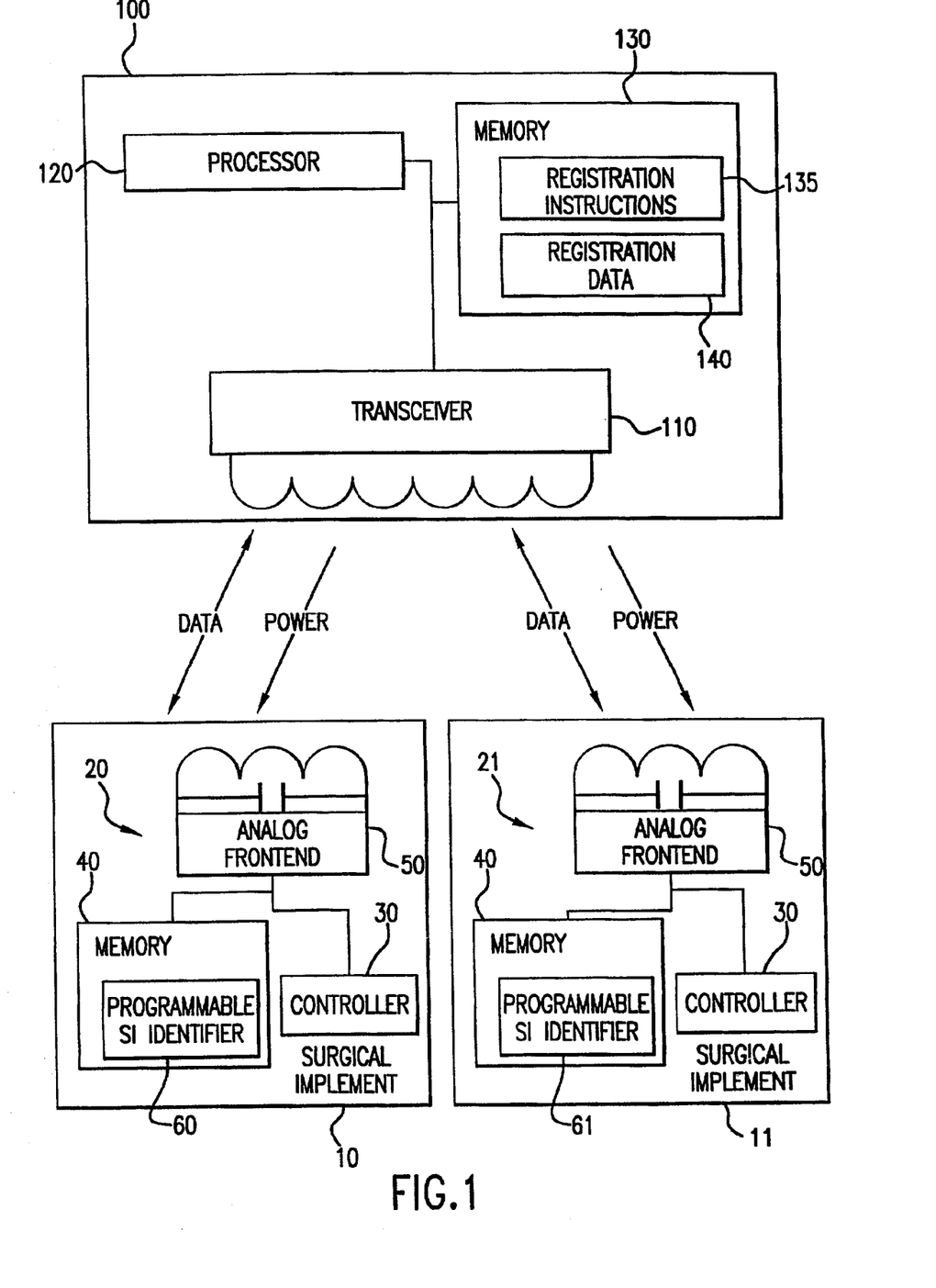
FIG. 1 shows a block diagram of the sensor system and two integrated circuits to be used in surgical implements.

FIG. 1 shows an example of one embodiment of the present invention. Like elements are labeled with like numbers. In FIG. 1, two surgical implements 10 and 11 are shown and a sensor system 100. Surgical implements, as used herein, include, but not limited to, sponges, needles, scalpels, gauze, forceps, and scissors and the like.

Also, the scope of the term surgery or surgical is not to be limited, but should include all types of medical procedures and is used herein interchangeably with the term medical.

In FIG. 1, surgical implement 10 includes an integrated circuit 20, and surgical implement 11 includes; an integrated circuit 21. The integrated circuit 20 includes an analog front-end 50, which could, for example, be a LC circuit; a memory 40; and a controller 30. In the memory 40 of surgical implement 20 there can be stored a programmable surgical implement identifier 60. This programmable surgical implement identifier is used as a unique identifier for each surgical implement. This particular illustration is but one example of how the present invention could be practiced and is not meant to limit the scope in any way.

The integrated circuits 20 and 21 are powered through radio frequency ("RF") signals generated by the sensor system 100. However, the integrated circuits may also be powered by any known source of energy, including, but not limited to, a battery, exposure to air, moisture, certain chemicals or substances, changes in temperature, pH, or motion. Additionally, the integrated circuits may be powered by induction, EMF, other radiation or by the potential, chemical, or electrical gradients, or micro-electric currents of the body.

The integrated circuits 20 and 21 are encapsulated in plastic and then incorporated into surgical implements. Generally, the integrated circuits are incorporated into each of the different surgical implements or materials natively. Therefore the integrated circuits are incorporated in such a way as to be encapsulated, hermetically sealed, flexible, heat, shock and water resistant and sterilized or sterilizable. The integrated circuits are also incorporated in a manner that does not impede or hinder the normal function of the medical implement. Because the surgical implements include many different instruments, incorporation of the integrated circuits into each different implement needs to be individualized to that implement and this can be done by those of skill in the art. Also, the integrated circuits can be incorporated into or structurally associated with x-ray opaque material.

FIG. 1 also shows a sensor system 100. The sensor system 100 includes a processor 120, a memory 130, and a transmitter 110. The memory 130 of the sensor system includes registration instructions 135 and registration data 140. The processor 120 can be a Pentium® III manufactured by Intel of Santa Clara, Calif., an Application Specific integrated circuit ("ASIC"), a microcontroller, etc. The registration instructions 135 will be explained more fully with reference to FIG. 5 and the registration data 140 will be explained more fully with reference to FIG. 3 and FIG. 4. The sensor system 100 may also include an interface consisting of a computer terminal or terminals (not shown). In addition, there may be additional, auxiliary sensory systems used in conjunction with the main sensor system throughout an operating room. Operating room as used herein, includes, but is not limited to, an operating theater, an operating room, an operating suite, or any other room where surgery or any invasive procedure of any type is performed on humans or animals.

One example of an integrated circuit and corresponding base station that a person of ordinary skill in the art could use to practice the present invention is TEMIC Semiconductors TK5552 transponder integrated circuit and base station, as described in TEMIC Semiconductors, "TK5552", Rev. A4, 26-April 2000, which is hereby incorporated by reference, in its entirety. TEMIC Semiconductors' TK5552 integrated circuit transponder is a programmable read/write transponder with an operation range of up to 10 cm powered by a RF field generated by the base station.

Other embodiments of the integrated circuit can be made of molecular switches using nanotubes as wires, such as described by Rotman in "Molecular Computing" *Technology Review* 103: 52–58 (May-June 2000), or molecular conductors such as benzine dithol as described by Reed et al. in "Computing with Molecules" *Scientific American*, 282: (June 2000), both of which are hereby incorporated by reference in their entirety.

In addition, the integrated circuit can be a RFID. The RFID may be readable only or readable and writeable. One example of an RFID that could be used in the present invention is disclosed in U.S. Pat. No. 6,249,227, hereby incorporated by reference, in its entirety.

Embodiments of the present invention relate to tracking and monitoring surgical implements. To that end, as can be seen in FIG. 1, data is read and written to and from the sensor system 100 and integrated circuits 20 and 21. The sensor system 100 assigns the programmable surgical implement identifier 60 to the surgical implement 10 and surgical implement identifier 61 to surgical implement 11 while collecting various data to compile the registration data 140 in the sensor system 100 and memory 130.

Figure 5:
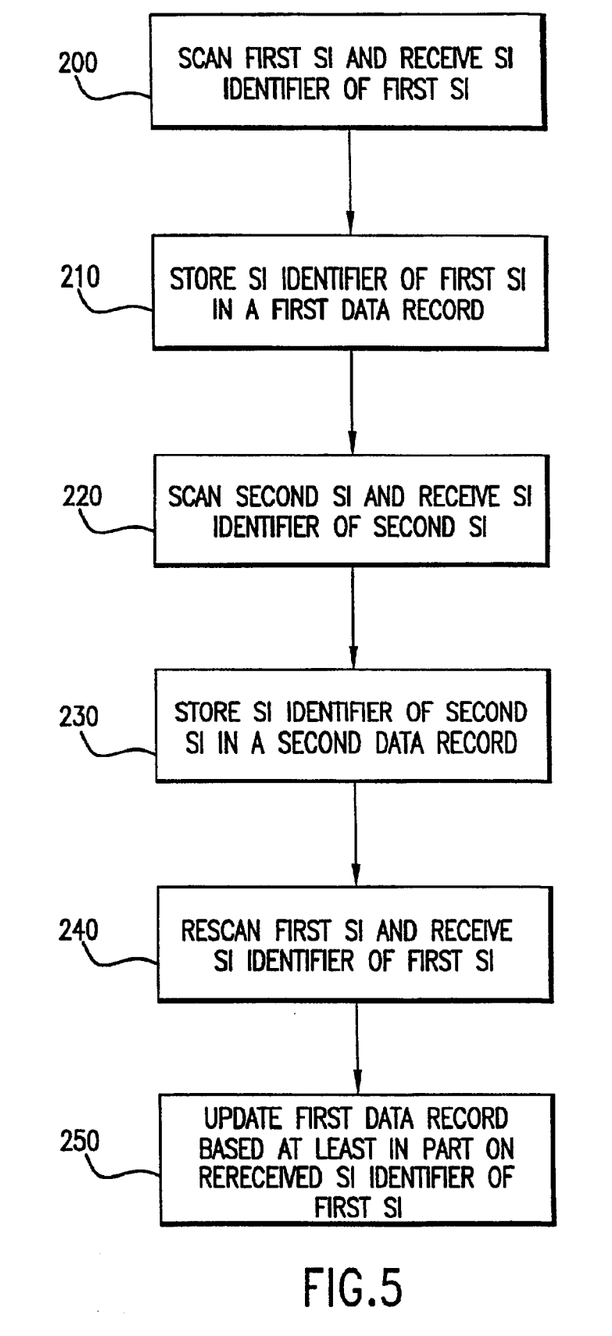
FIG. 5 shows a flow chart of registration instructions for the sensor system.

An example set of registration instructions 135 stored in the memory 130 of the sensor system 100 is shown in FIG. 5. In the first step 200, the sensor system 100 scans a first surgical implement and receives the surgical implement identifier of the first surgical implement. At step 210, the surgical implement identifier of the first surgical implement is stored in the registration data 140 in the memory 130 of the sensor system 100 in a first data record. In step 220 the sensor system 100 scans a second surgical implement and receives a surgical implement identifier of the second surgical implement. At step 230 the surgical implement identifier of the second surgical implement is stored in a second data record in the registration data 140. In step 240 the sensor system 100 re-scans the first surgical implement and re-receives the surgical implement identifier of the first surgical implement. In step 250 the first data record is updated based at least in part on the re-received surgical implement identifier of the first surgical implement.

Figure 3:
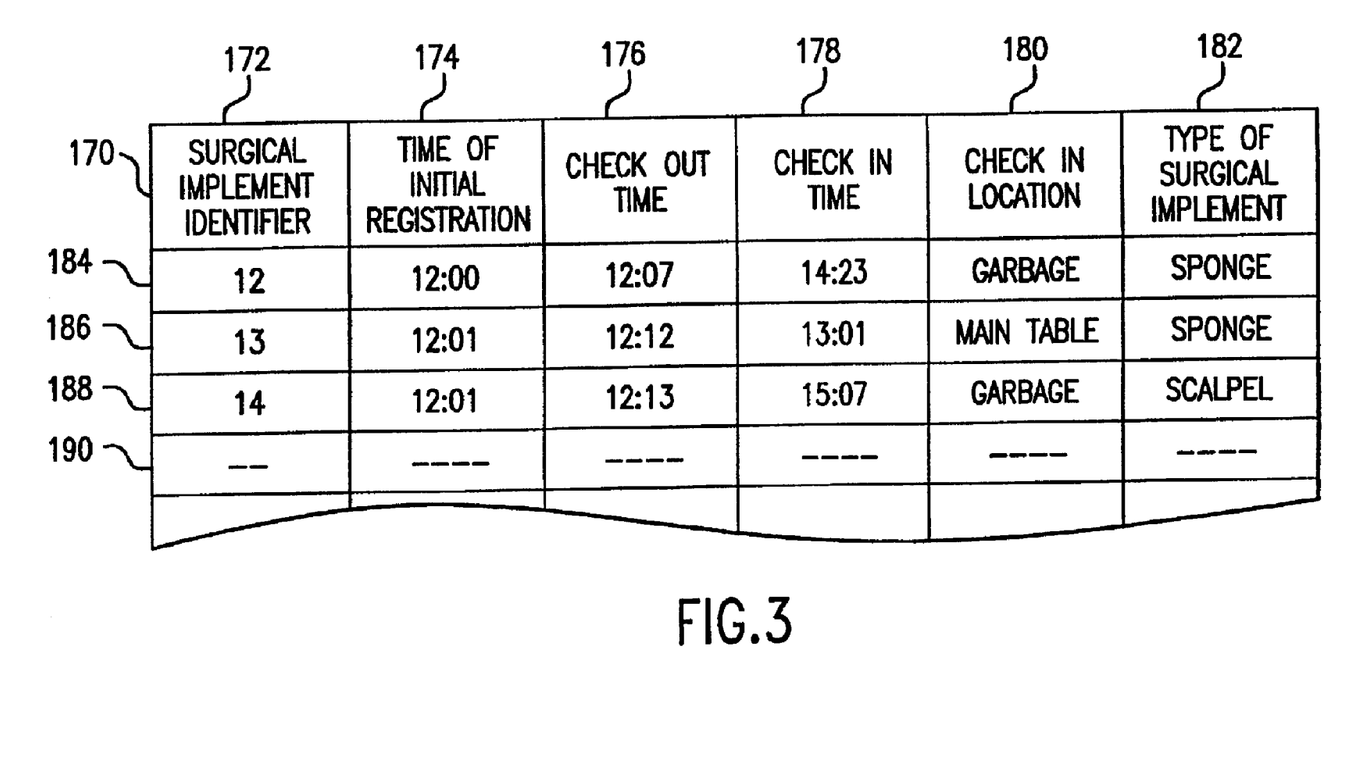
FIG. 3 shows an embodiment of a database table for the sensor system.

The registration data 140 can be a relational database 170 shown in FIG. 3. Database 170 includes records 184–190, which are accessible using a suitable database management system software. Each record 184–190 of database 170 contains six fields 172–182. Field 172 holds the surgical implement identifier, which can be any unique identifier, for example a number(s), letter(s), a combination of numbers and letters, a frequency, or the like. In this embodiment, the memory 40 of the integrated circuit 20 is programmable, so the surgical implement identifier 60 is programmable. Therefore, field 172 can be programed by the sensor system. Field 174 indicates the initial time of registration, for example when the sensor system first senses the surgical implement and is associated with a registration identifier. Field 176 indicates when the given surgical implement was checked out to be used in a surgery and is associated with a checked-out identifier. Field 178 holds information about when the given surgical implement was checked back in following it use and is associated with a checked-in identifier. Field 180 holds information about the check-in location within the operating room and field 182 indicates what the actual surgical implement is, for example, a sponge, a scalpel, gauze, or the like. This particular arrangement of fields is but one illustration of how the invention may be practiced. For example, certain fields can be omitted, additional fields can be provided, or the arrangement of fields can be changed. For example, additional fields for the check-in or check-out location can be added. Also, a field could be added that indicated the count of each implement.

For example, that a particular sponge was sponge five of twenty-5/20 or that a scalpel was two of five-2/5.

Each record 184–190 of database 170 associates a surgical implement identifier with time of check-out and time of check-in. In addition, other information is associated with each surgical implement, for example, the actual surgical implement and the location of its check-in. By compiling this information it becomes possible to monitor each individual surgical implement.

Figure 2:
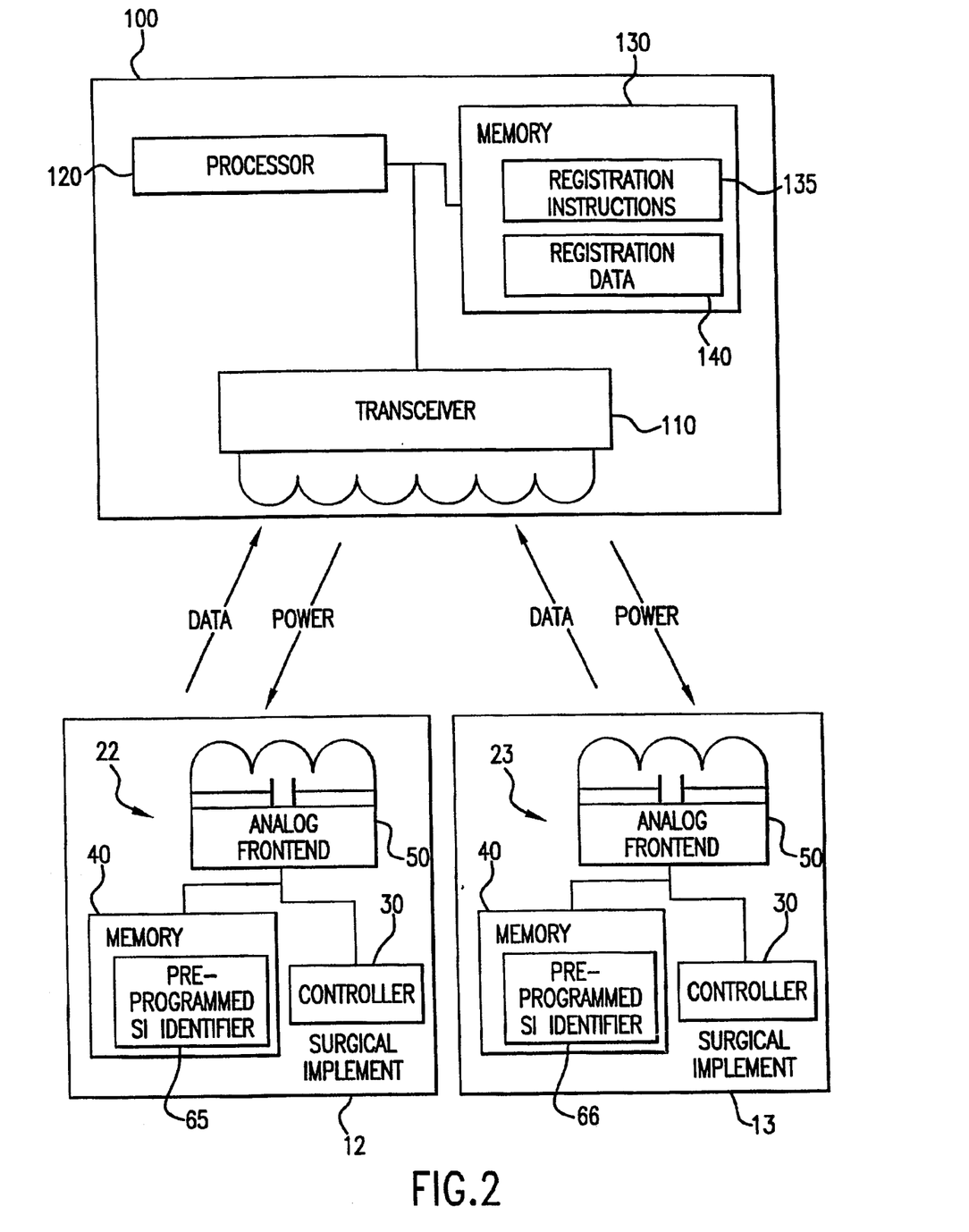
FIG. 2 shows a block diagram of the sensor system and two integrated circuits to be used in surgical implements.

FIG. 2 shows a similar embodiment as FIG. 1, except that the data is only shown being read by the sensor system 100. The memory 40 of the integrated circuit 22 has a pre-programmed surgical implement identifier 65 as compared to the programmable surgical implement identifier 60 of FIG. 1, and integrated circuit 23 has a pre-programmed surgical implement identifier 66.

Figure 4:
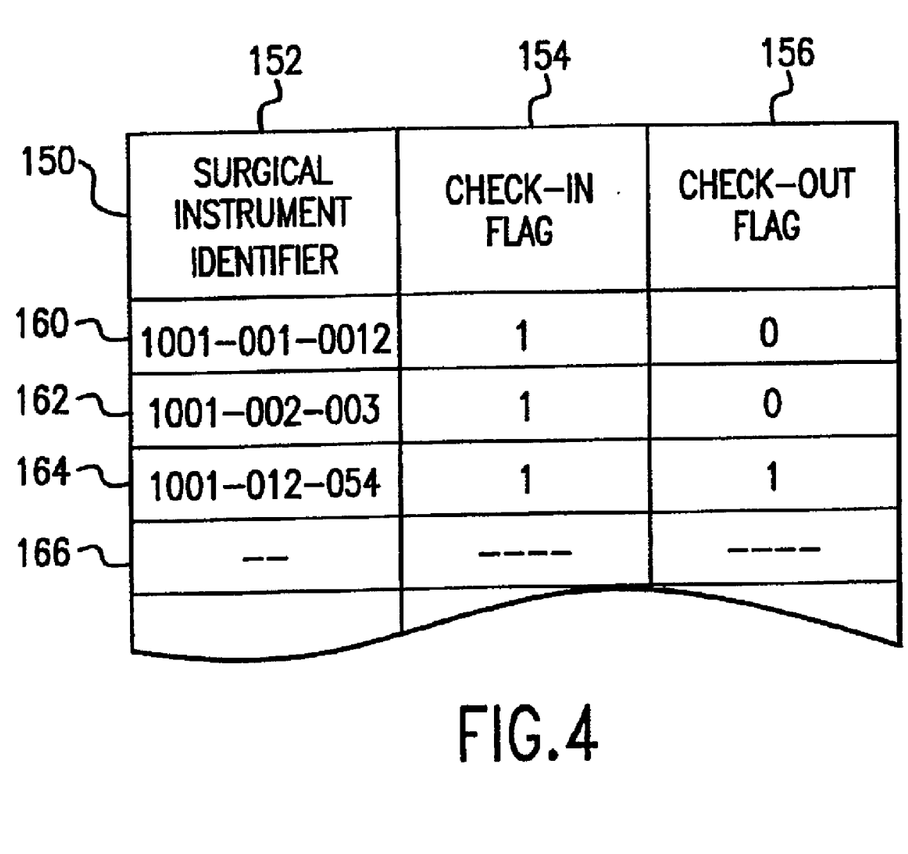
FIG. 4 shows an embodiment of a database table for the sensor system.

FIG. 4 shows database 150, which could be used with the embodiment of the present invention shown in FIG. 2. Database 150 includes records 160–166, which are accessible using a suitable database management system software. Each record 160–166 of database 150 contains three fields 152–156. Field 152 contains the surgical implement identifier, which is pre-programed in the surgical implement. The preprogramed identifier could be programed, for example, in such a way as to indicate the hospital, the type of implement, the number of the implement, or other parameters desired to be associated with the implement. This particular programing is one illustration of how the invention may be practiced. Field 154 corresponds to a check-in "flag" if the surgical implement has been taken to be used, while field 156 corresponds to a check-out "flag" when the surgical implement is brought back after being used. This is a simplified version of the database shown in FIG. 3.

Prior to surgery, each surgical implement having an integrated circuit in it is placed on or near the main sensor system. The sensor system assigns an individual surgical implement identifier to each surgical implement and records initial data (e.g., initial time of registration). In order to make sure that no unregistered implements are located within the operating room, the sensor system will note all incomplete implement integrated circuit data profiles and alert upon such sensing. When the surgery begins and the surgical implements are used, the sensor systems records the time each surgical implement is checked-out/used. When the surgical implement is done being used and the surgical implement is replaced either on or near the main sensor system or in an auxiliary sensory system, the time and optionally, the location, of check-in for each surgical implement is recorded. Following surgery, a comparison is completed of surgical implements checked-out and surgical implements checked-in and a list is generated to identify which surgical implements are missing, if any. An output device, such as a computer can be used to display the list. In addition, an alarm will sound if any surgical implements are checked-out but not checked back in from the sensor or the output device. Alternatively, the sensor system can keep a running comparison of the surgical implements that have been checked-out and the ones checked-in. In this manner the sensor system can be programmed to alert at particular times during the procedure in order to track the surgical implements throughout the procedure.

The functions of the sensor system include, but are not limited to, sensing, tracking, marking, managing, monitoring, setting, controlling, checking, dating, timing, billing inventory control and comparing with protocol. When the implements are placed on, in, or near the main or auxiliary sensor system, each is detected and assigned a unique and individual identifier by the associated sensor system. The identifier used herein includes, but is not limited to, information regarding the product, numbers, strings of letters and numbers, strings of letters or other codes, or a frequency. The sensor system and the auxiliary sensor systems as used herein include, but are not limited to, handheld devices, perimeter systems, entry/exit systems, tables, trays, shelves or stands.

In another embodiment, a backup system could be incorporated into the surgical implements using a second integrated circuit, or tag, which would generate an error message when read by a sensor system if there was a problem with a primary integrated circuit.

In another embodiment, the initial assigning of surgical implement identifiers is performed when the surgical implements enter the operating room.

Figure 6:
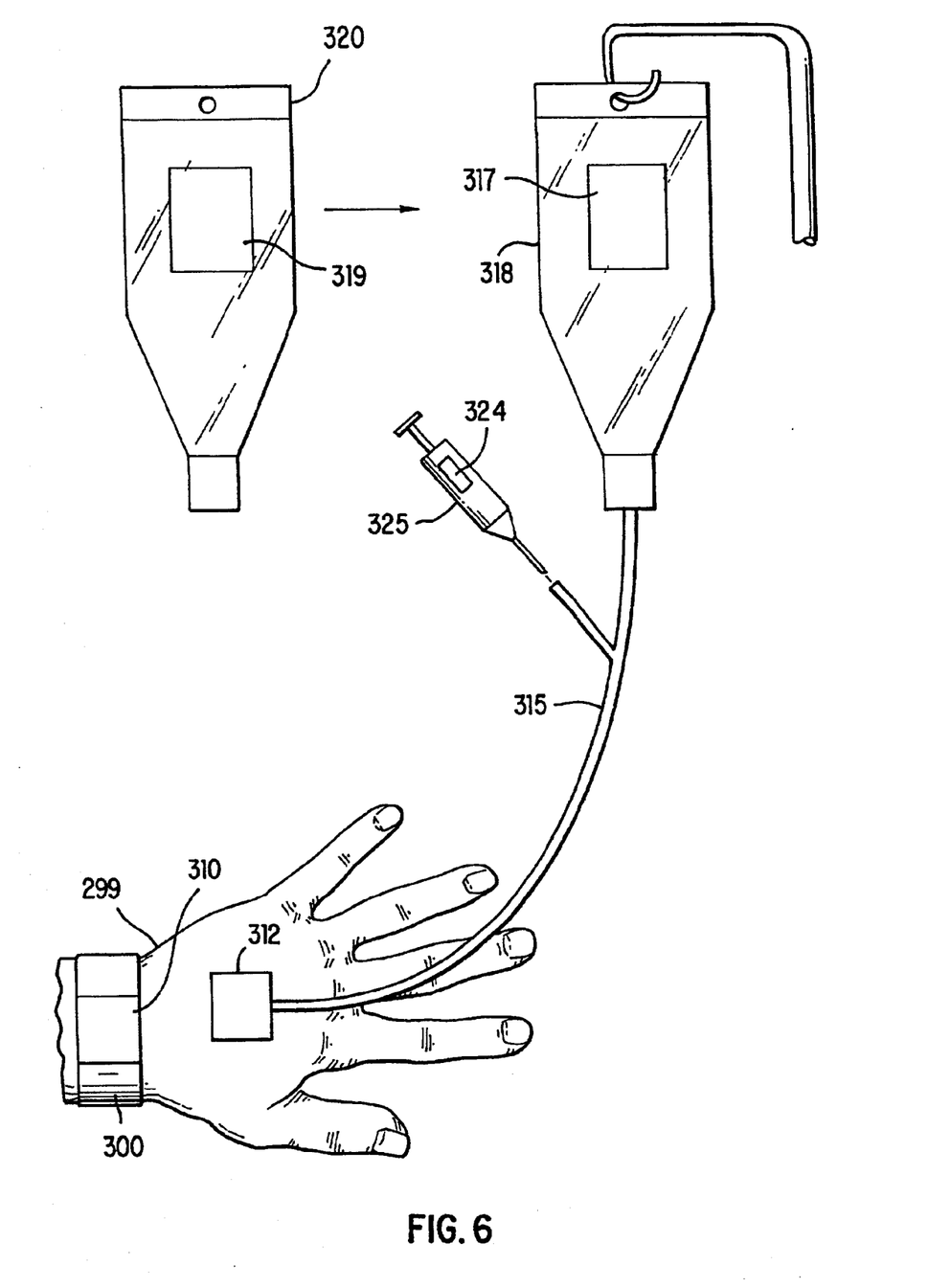
FIG. 6 shows an embodiment of the sensor system in a patient ID bracelet and integrated circuits in blood bags and syringes.

FIG. 6 shows another embodiment of the present invention. A patient 299 wearing an identification bracelet 300 is receiving fluids, medication, or blood 318, through tubing 315, intravenously 312. The identification bracelet 300 contains a sensor system 310, which includes information about the patient 299, including allergies, medical orders, medication orders, and the like. Each of the bags 318 and 320 include integrated circuits 317 and 319 respectively, which may be placed directly on the bags 318 and 320 or incorporated into a label and then placed on each bag 318 and 320. The integrated circuits 317 and 319 indicate what is in the bags, either blood, medication, fluids, etc. Likewise, syringe 325 contains medication and includes an integrated circuit 324, which indicates what medication is in the syringe 325. If the contents of bag 320 or syringe 325 are harmful, potentially harmful, or inappropriate in any way for patient 299, then when the integrated circuits 319 or 324 come near the sensor system 310 located in the patient's identification bracelet 300, an alarm/alert (not shown) will sound. In an alternative embodiment, the sensor system can be located elsewhere in the patient's room. In addition, more than one integrated circuit can be located on or around the patient. In another embodiment one or more integrated circuits can be sensed by a sensor system and then the associated information from each integrated circuit is compared to the other or alternatively to stored information. If the information does not match a given set of parameters, an alert or alarm will sound.

In another embodiment of this invention, medical orders, such as for medical procedures, laboratory studies, or the like, are tagged with one or more integrated circuits—integral or removable, and a sensor system is located on or near the patient or in the patient record, card, chart, or hand held, or other computing platform. In another embodiment, the sensor system or sensor auxiliary device is located in the patient identification bracelet, dog tag, or other suitable appliance.

The patient sensor system is preprogrammed with patient information, including, for example, allergies, current medications, medical problem list, patient requests, consents, date of birth, name, insurance, next of kin, contact information, and the like, and may be programmed with status updates or orders. If an inappropriately tagged blood product or drug is brought in proximity to the patient, the sensor will trigger an alert or alarm which can take many forms for easy identification. Similarly, if a disposable integrated circuit card, for example, a 2" by 3" plastic card (i.e. credit card size) in which an integrated circuit was embedded, for each procedure is generated, should an orderly carrying this card approach the wrong patient for transport, an alert will be generated. The integrated circuit can be, for example a flash memory card or a smart card.

In another embodiment, a second integrated circuit can be located in the patient identification bracelet or dog tag. If both the medical orders and the patient identification bracelet contain integrated circuits, then the sensor system can monitor and track whether two integrated circuits move too close together, for example, if the wrong medical orders were about to be placed in a patient's chart or the wrong medicine was to be given to a patient. In this embodiment, the sensor system can indicate a conflict between two integrated circuits visually or audibly. In addition, an output device, such as a monitor, can display which devices are in conflict.

In yet another embodiment of this invention, pharmaceutical products have one or more integrated circuits attached to the containers, bottles, bags, or labels which may be integral or removable for attachment to inventory lists, patient charts or intravenous ("IV") or injection apparatus as noted above. Remote sensors on hand held devices, located in cabinets where pharmaceuticals are stored, or situated elsewhere, can quickly identify expired or misplaced or otherwise inappropriate drugs. Effective tracking of inventory with appropriate software is improved and appropriate ordering, billing and analysis of other information are enhanced.

In another embodiment of the present invention, a medical label includes at least one integrated circuit. The medical label can also be just the integrated chip. In addition, there can be more than one label on a given medical product. The medical label can be used to label any type of medical material or product, including pharmaceutical products and blood products, for example as shown in FIG. 6. The medical label can also be placed on medical containers, such as boxes, boxes that contain medical products, crates that contain medical products, bottles, ampoules, bags, syringes, or the like. The integrated circuit within the medical label can include information about the origination of the medical product, verification information about the medical product, the destination of the medical product, what the medical product is, which patient is to receive the medical product, indications, contra-indications, interactions, or similar medically or logistically relevant information. The verification information can include data that indicates the authenticity of the medical product. In addition, there can be more than one medical label on a given medical product. For example, an integrated circuit as described (either in a label or as the label itself) can be used and at least one additional label in the form of a written description of the medical product can be also located on the medical product.

In another embodiment where the medical label is used to label blood products, the integrated circuit can include collection, processing, storage, distribution, usage, and patient delivery information. Collection, processing, storage information, usage and the like can include, information about the blood donor, the blood type, blood recipient, expiration date, unit number, antigens, antibodies, logistical information, delivery distribution, or combinations thereof.

In addition, the label can have certain physical and chemical properties. For example, the label can be temperature resistant, water resistant, shock resistant, and flexible. The integrated circuit within the label can be hermetically sealed so that the environmental conditions experienced by the label do not effect the integrated circuit. For example, such environmental conditions can include the blood container containing the label being frozen and then thawed for storage purposes. The blood products referred to in these embodiments can include, but are not limited to, whole blood, platelets, packed red blood cells, and plasma.

EXAMPLE

A patient is prepped for a surgical procedure and brought into the operating room. The operating room team comprising, for example, three operating room nurses, two doctors, and an anesthesiologist are also present in the operating room. The operating room nurses are responsible for, among other things, tracking the sponges, scalpels, gauze, forceps, clamps, and other medical implements used during the surgery or surgical procedure. To this end, each surgical implement to be used in this surgery includes an integrated circuit. As the nurses prepare for the surgery, they place each of the surgical implements on or near a sensor system, which is located near to the operating table upon which the patient lies. This sensor system registers each of the implements. As each of the implements is registered, the nurses watch the information appear on a screen of the sensor system, (e.g., a display of a computer) for each of the implements: 1) what each implement is; 2) the time the implement is placed on the sensor system; 3) the place where the implement is being registered; and 4) a unique identifier assigned to each implement is shown. Once all of the implements have been registered, the surgery can begin.

The doctors begin the surgery and each implement is used in turn. As each implement is used by the doctors, it is removed from the proximity of the sensor system. For example, when one of the nurses hands a scalpel to a doctor, the sensor system senses that the scalpel has been "checked-out" at a certain time. When the doctor has finished with the scalpel, a nurse can either put the scalpel back near the sensor platform it was removed from or place the scalpel on or near an auxiliary sensor system (e.g., a sharps container). When, for example, the auxiliary sensor system senses the scalpel, the scalpel is registered as "checked-in" and the location and time of check-in is also noted.

For each surgical implement, each of these steps can be performed. However, if at the end of the surgery, there are implements that have not been checked-in, then the sensor system indicates which implements are missing (e.g., not checked-in). In addition, prior to the doctors suturing the patient, a nurse checks the sensor system (e.g., the display of the computer mentioned earlier). In another embodiment, the sensor system can sound an alarm to remind the operating room team that there are implements missing.

Once the operating room team is aware that there are items missing and what items are in fact missing by looking at the information provided by the sensor system (e.g., the display of the computer again) as to the description of the item, the check-out time, and the like, a doctor can use an auxiliary sensor system in the form of a portable sensor system to locate the implement. For example, if the implement is still within the patient, a portable sensor system comparable to sensor system 100 but portable in nature is used to locate the missing implements.

Conclusion

Embodiments of devices, methods, systems to surgical implements and other medical products, including integrated circuits have been described. In the foregoing description, for purposes of explanation, numerous specific details are set forth to provide a thorough understanding of the present invention. It will be appreciated, however, by one skilled in the art that:the present invention may be practiced without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the present invention.

Further Embodiments

Other embodiments of the present invention are directed to electronic devices and their use for tracking medical products such as medications, blood, and tissue to improve patient safety. The embodiments utilize electronic devices including but not limited to RF ID (radio frequency identification) devices which are attached to the medical products to assist in their safe production, distribution, and administration to patients. These devices may be programmed with information which is pertinent to the proper identification, routing, and administration of the medical products. The information may subsequently be read at any time during the life cycle of the medical product. In a particular embodiment, the information is routed to computing systems where it may be processed.

Medications:

One embodiment of the invention uses RF ID devices such as labels or tags for medications. The devices may be placed by any known process on containers, vials, ampules and the like. In one embodiment, commonly used labeling information is visibly readable on each label or tag. At the point of manufacture, the labeling process involves applying one or more labels having RF ID devices to the unit dose container. Ideally, one or more of these RF ID devices will be adhesive and removable for subsequent attachment to IV bags, syringes, patient charts; smart cards and the like. In one embodiment these devices are very thin, flexible, resistant to extremes of temperature, moisture, trauma and have a shelf life greater than four years. The devices may be readable and/or printable and may, for example, contain certain data which may include but not be limited to, drug type, name, formulation, interactions, dosages, expiration date, batch number, location of manufacturing facility and contraindications. As the individual unit doses are packaged, each packaged grouping also includes one or more labels having RF ID devices attached to its larger subpackage with all the information found in each individual unit dose and with the number of individual units contained in each package or subpackage. Hence, a large package or shipment of drug can have multiple RF ID devices arranged in such a way that each subpackage is accounted for individually and sequentially with the RF ID device of larger units accounting for the next level of smaller units. This pyramid design provides consistency and better tracking ability as the units are easily referenced to larger master RF ID units.

After the application of the devices to the pharmaceutical products, sensors note the distribution of the products through the facility and their exit as they are shipped to wholesalers or distributors, or to healthcare facilities. Appropriate data is recorded and stored centrally. As the products reach their destination they are data scanned and this information is again centrally processed. The products are then routed to the appropriate final locations, where they are kept in the pharmacy or sent to patient care areas. While there, essential data is recorded locally and centrally. The use of scanners, which may be portable or fixed, within storage cabinets or other fixtures keeps track of inventory and note the presence of outdated drugs for easy disposal. Further, the presence nonformulary products or concentrations as well as other inappropriate medications can be made known to responsible parties in a timely and effective manner. The presence of an LED, which could be programmed to emit light when expiration has occurred, or which could be induced to emit light when an external field is applied to an RF ID device on an expired drug package, would make identification even easier.

When an order for drug is received this too can be programmed electronically such that the correct drug is automatically selected from a central distribution center or from a local drug access center. Here, the RF ID device could also assist in correct drug selection. When the correct package is chosen, relevant data is recorded for billing, inventory, and related referencing and for comparison with patient data to avoid allergic reactions, redundancy, and possible adverse interactions.

At this point, one RF ID device may be taken from the unit package and placed on the patient record, chart, or smart card. A second RF ID device which also has written drug data as to drug name, date of administration and concentration should be adhered to a syringe or IV bag. In a preferred embodiment, a smart card, chart, or ID band would have an RF ID or other device containing relevant patient history, treatment, orders and other data and would be updated real-time or on a frequent basis. A sensor/processor unit compares the data from the ID devices of the drug and the patient. This helps ensure that compatibility exists and the therapy is appropriate. In one embodiment, an enabling signal precedes therapy, and a failsafe signal is generated to alert appropriate parties that a level of patient safety is breached. The sensor processor unit can be integral with the patient RF ID tag, for example on the patient ID bracelet, with the ability to transmit to a central computer or processor, or it may be physically separate as a stand alone device or one receiving and relaying data to a central location. The sensor/processor device may be linked to central data and computer systems by wireless or other commercially available means.

Blood/Tissue Products:

Other embodiments of the invention disclose the use of RF ID devices in processing and administering blood products and the transplantation of tissue products to human patients. At the point of collection, one or more RF ID devices are appended to the collected blood. Relevant data is encoded on them as to collection time and date, typing or other essential data, method of viral inactivation and the like. Alternatively, a radio frequency bar code may be used. If the blood is fractionated, one or more RF ID devices are attached to each derived unit of product. This is done in such a way that all the data contained in the first RF ID application are contained in all subsequently written RF ID labels with the relevant new data for the derived products encoded or written subsequently. Hence, products can be tracked easily back to the original donor and source. The RF ID devices are able to withstand the processes required for the preparation of safe blood products and their derivatives. Hence, the RF ID devices are water resistant, resistant to physical stresses and the extreme cold used in the storage of blood products. They generally have long shelf lives, but this is unnecessary for packed red blood cells. Encapsulation may be used to add to their durability, and the RF ID devices can be thin, flexible, adherent and easily removable and reattachable. One of the series of applied RF ID devices serves as the master RF ID and is undetachable except through removing the RF ID device from the adherent portion allowing its inclusion to a master database after use.

A central sensor is able to distinguish among the units stored in a single location and individually track their data. Hence, real-time inventory is achieved.

When units and products are distributed, their routes and destinations are noted and recorded. On arrival to a hospital or other healthcare facility, a sensor confirms their arrival and records the data. This can be relayed back to the place of origin for confirmation. Once again, a sensor distinguishes among the many different units stored in one location and that information is stored centrally. If other typing is done, that data is added to the RF ID labels on the appropriate units. When the hospital types or screens a patient for the receipt of the product, that information is centrally stored and the chosen units have their RF ID tags updated and further encoded with that additional patient data.

Alternatively, a second series of RF ID tags can be generated and applied to the appropriate units. Electronic or other mechanical or functional linkage can be used. When a unit of product is ordered, the information is recorded centrally. When the unit of the product arrives at its destination, it is again sensed and appropriate data is displayed. When the unit is taken for patient administration, this is noted by the local sensor and relayed centrally. When the unit is taken to the patient, another patient specific RF ID, or other device, on a patient ID bracelet, smart card or chart or nearby allows for comparison between the patient data and the product data. The sensor/processor can be integral to the patient specific RF ID device or separate in a local or central locale as noted above. Before administration, positive enablement can be achieved. A failsafe mechanism signals an alarm if any incompatibility is present, providing passive security. This process facilitates processing, distribution, record keeping, inventory, billing, and improves patient safety and decreases product waste.

Figure 7:
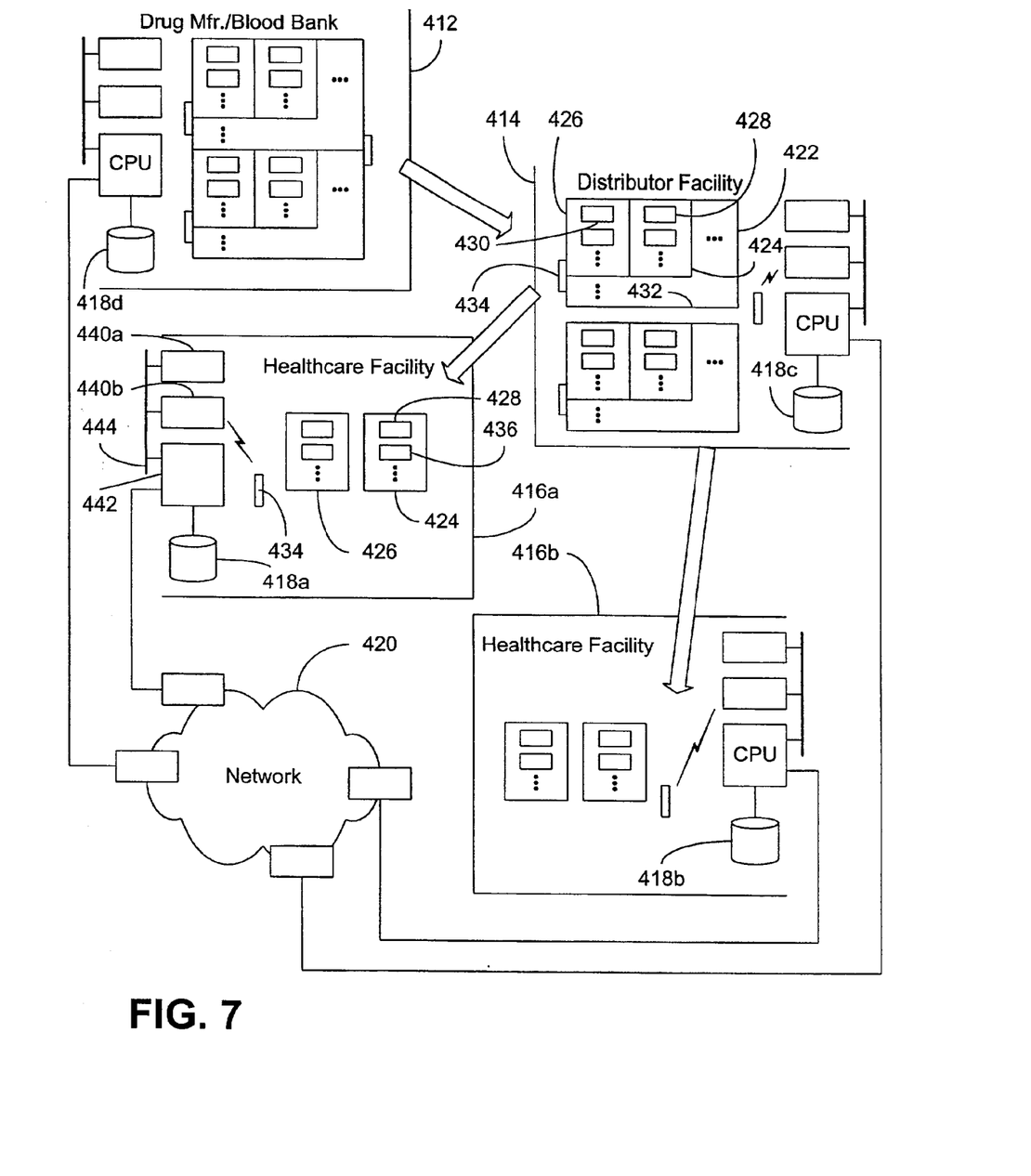
FIG. 7 shows a diagram of an example of a medical product infrastructure utilizing an assembly of medical products in accordance with one embodiment of the invention.

FIG. 7 shows an infrastructure 410 in which the principles described herein can be useful. Generally, it will be appreciated that throughout the life cycle of a medical product, a number of entities/facilities may be involved. For example, a source facility 412 such as a drug manufacturer or blood bank may transport the medical product to a distributor facility 414, where the distributor facility 414 distributes the medical product to one or more health care facilities 416a, b, etc. As will be discussed in greater detail below, each facility maintains a central database 418a–418d of source data and/or patient, where each database 418a–418d may be accessed by the other facilities in the infrastructure 410 via network 420.

By way of example, it can be seen that an assembly 422 of medical products includes a first unit 424 and a second unit 426. The first unit 424 of the medical product includes a first unit RF ID 428, which may be incorporated into a label as discussed above. The first unit RF ID 428 uniquely identifies the medical product and the first unit 424. Similarly, the second unit 426 of the medical product has a second unit RF ID device 430 where the second unit RF ID device 430 uniquely identifies the medical product and the second unit 426. It can further be seen that packaging 432 such as shrink wrapping, box or crate, combines the first unit 424 and the second unit 426 into a group. Furthermore, the packaging 432 has a group RF ID device 434, where the group RF ID device 434 uniquely identifies the medical product, the first unit 424 and the second unit 426. It will be appreciated that the medical product can include pharmaceutical products, blood products, tissue products, or any combination thereof. It should also be noted that the group identified by the group RF ID device 434 typically includes many more units than the two illustrated.

It will further be appreciated that a first supplemental RF ID device 436 may be removably attached to the first unit 424, where the first supplemental RF ID device 436 also uniquely identifies the first unit 424. This allows the first supplemental RF ID device 436 to be subsequently reattached to other containers such as vials, syringes, etc. if the first unit 424 is fractionated. Similarly, a second supplemental RF ID device 438 may be removably attached to the second unit 426. The second supplemental RF ID device 438 uniquely identifies the second unit 426. The supplemental RF ID devices may be applied at the source facility 412, the distributor facility 414 or anywhere else in the distribution chain of the medical product.

As already discussed, the RF ID devices may include source data and unit number data. In the case of pharmaceutical products, data may include but is not limited to drug-type data, drug-name data, formulation data, interaction data, dosage data, expiration data, batch number data, indication data, carton indication data, or combinations thereof. In the case of blood products, data may include, but is not limited to blood donor data, blood type data, expiration data, antigen data, antibody data, or combinations thereof.

It can further be seen that facilities such as health care facility 416a may include one more sensing systems 440a, b, etc. in communication with the RF ID devices 428, 430, 434, 436, 438 and a central processing unit (CPU) 442. While communication is illustrated as being implemented via a bus network 444, it will be appreciated that any appropriate local area networking (LAN), wireless networking, or other architecture may be used. It can be seen that the CPU 442 is coupled to the central database 418a and associates the received data in accordance with any number of commercially available database approaches.

Figure 8:
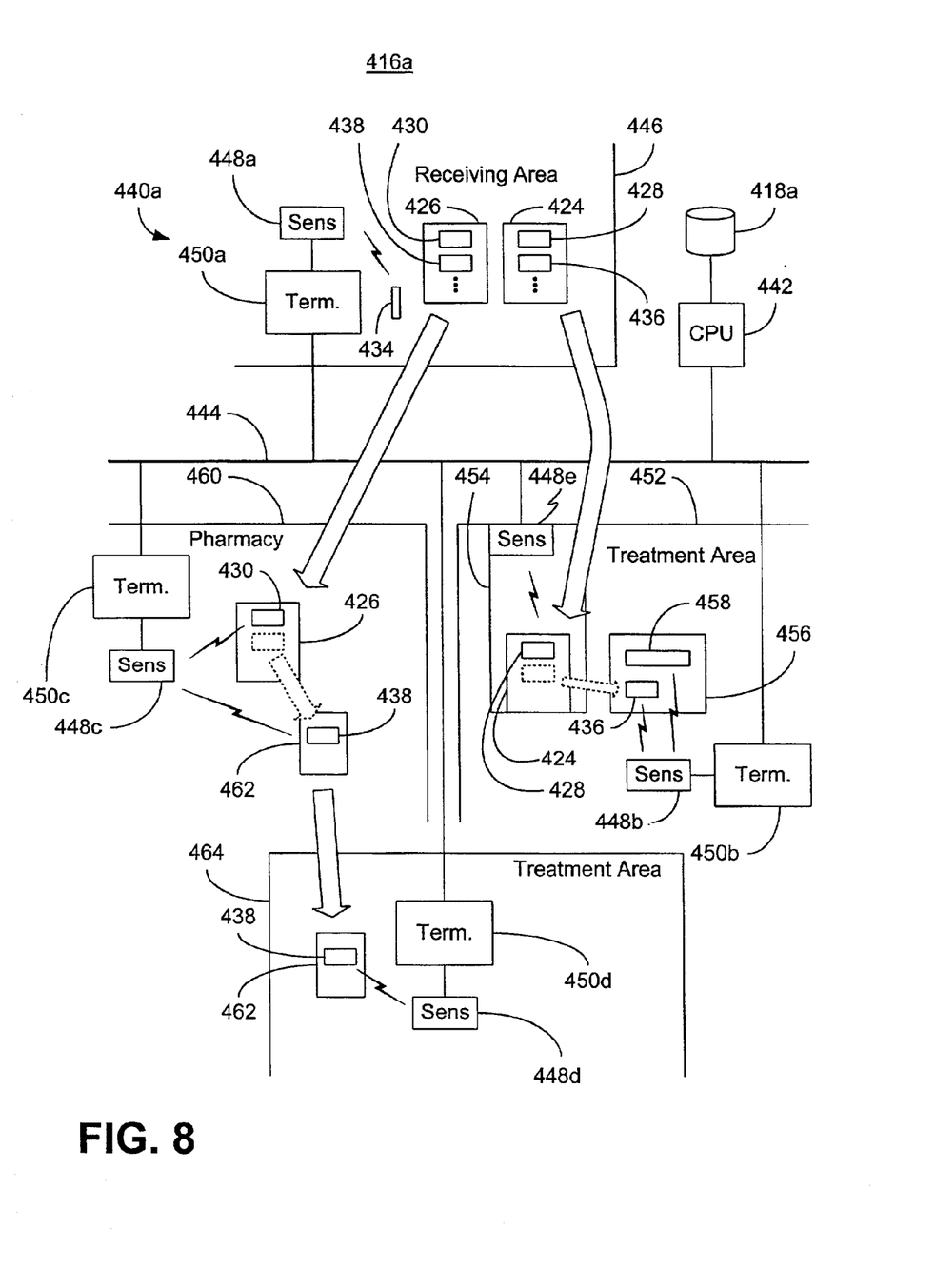
FIG. 8 shows a diagram of an example of a health care facility utilizing an assembly of medical products in accordance with one embodiment.

Turning now to FIG. 8, health care facility 416a is shown in greater detail. Specifically, it can be seen that the assembly of medical products enters the health care facility 416a at receiving area 446. The group RF ID device 434 is scanned using sensor 448a in order to log the uniquely identified first unit 424 and second unit 426 in as being received. This enables unit data and source data to be associated with any patient data/location data that may be entered into computing terminal 450a. This information is transmitted to the CPU 442 for storage in the central database 418a.

It can be seen that as the units 424, 426 move throughout the health care facility 416a, the overall system enables tracking of such movement as well as updating of any relevant patient data using, for example, sensors 448a–448d and terminals 450a–450d. For example, in the illustrated example, the first unit 424 is sent to a treatment area 452 and is placed in a pharmaceutical cabinet 454 for temporary storage. Before placement in the cabinet 454, the first unit RF ID device 428 can be scanned by sensor 448b, where the treatment area location is associated with the first unit 424. Additionally, the first unit RF ID device 428 may communicate with a sensor 448e mounted within the cabinet 454. It can further be seen that a patient chart 456 has a patient data RF ID device 458. In the illustrated example, the first supplemental RF ID device 436 may be attached to the patient chart 456 and any conflicts can be detected and reported as discussed above.

It can further be seen that second unit 426 is sent to a pharmacy 460 for storage until an order is placed for the particular medical product. It can be seen that if the second unit 426 is fragmented to a supplemental container 462, the second supplemental RF ID device 438 can be attached to the supplemental container 462 in order to document the fragmentation. Thus, when the supplemental container 462 is sent to treatment area 464, sensor 448d and terminal 450d can initiate an update of the central database 418a.

Figure 9:
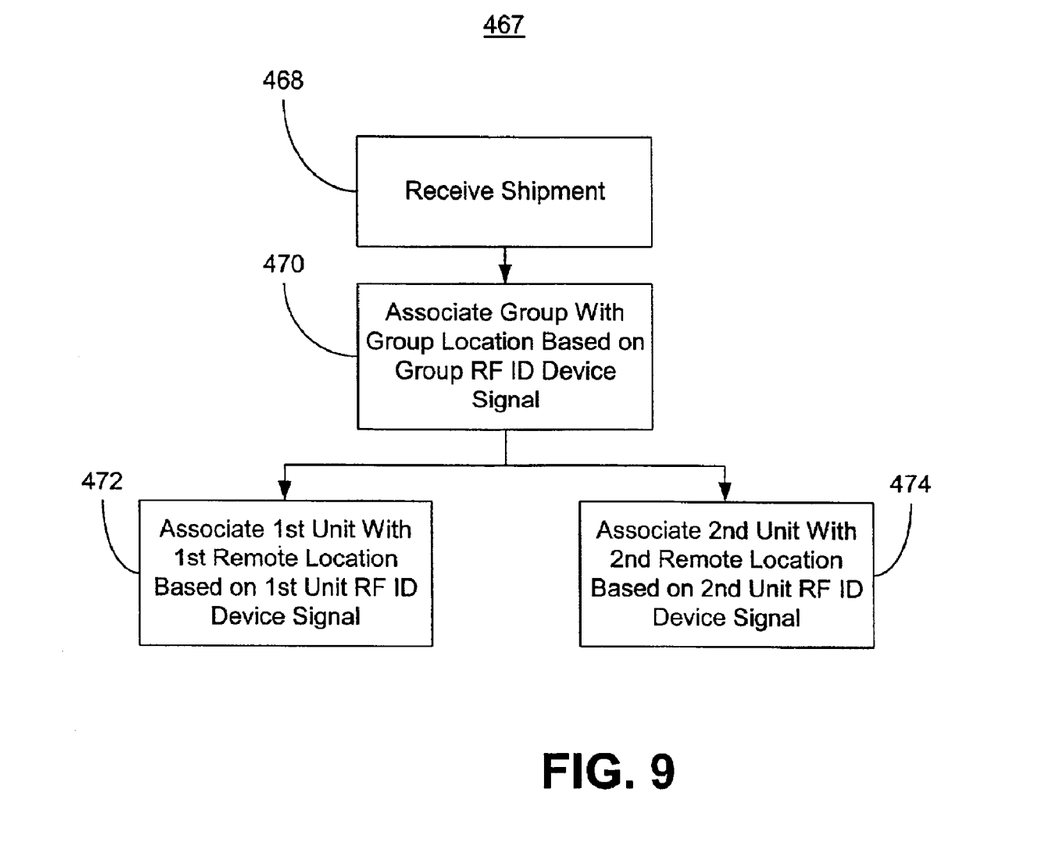
FIG. 9 shows a flow chart of an example of a method of tracking medical products in accordance with one embodiment of the invention.

Turning now to FIG. 9, a method 467 of tracking medical products is shown. Processing block 468 provides for receiving the shipment, which contains the assembly of medical products. A group of medical products is associated with a group location at block 470 based on a group RF ID device signal. As already discussed, the group includes a first unit and a second unit. Block 472 provides associating the first unit with a first remote location based on first unit RF ID signal. The second unit is associated with a second remote location at block 474 based on a second unit RF ID device signal. The signals uniquely identify the units and the group.

Example Scenarios

The following scenarios illustrate by way of example certain of the principles of the embodiments of the present invention:

Scenario #1

A widely used medication is received by a hospital. A tracking device in accordance with the present invention is affixed to each vial of the medication, and the vials are distributed to various locations within the hospital. Prior to distribution, tracking information such as product type, name, formulation, interactions dosages, expiration date, batch number, manufacturing facility, handling and storage information, and distribution locations are entered into a central computer. At a later date, it is discovered that the expiration date of the medication is in error, and that it will shortly expire. Using the information stored in the central computer, the locations of the medication are rapidly determined, so that removal and disposal can be achieved. Alternatively, a sensor in a storage cabinet periodically scans all medications and directly identifies the presence and location of the expired drug. It is also possible to have a pre-programmed timer, clock or a chip or other circuit such that an individual RF ID device independently emits a signal when a certain date is reached which may be noted with a passive or active sensor array or by a characteristic sound, light or electrochemical color change of part or all of the printed label or package. A battery source set to expire at or near the expiration date of the pharmaceutical may also be used, wherein when the battery source expires an alert is issued.

Scenario #2

A patient is to undergo emergency surgery immediately. Information, including that relating to the patent's allergies or other drug reactions is written on the patient's RF ID bracelet in accordance with embodiments of the present invention. In the operating room just prior to surgery, the anesthetics to be used during the operation are automatically scanned and this information was processed with the information on the ID bracelet. It is discovered that one anesthetic agent would produce a severe reaction in the patient. A safe substitute anesthetic is suggested by the system and was subsequently used during the procedure with good result.

Scenario #3

A patient arrives at the ER complaining of vomiting blood. A type and cross is sent immediately and information is encoded and written on the central computer and on the RF ID label directly and immediately placed on the ER patient's sample tube at the point of blood sampling. This tube arrives at the hospital blood bank where it is scanned to avoid clerical and other errors involving patient data. The central computer has already used the patient data to access previous data from prior hospital or clinic visits, and may use the internet or other known modality to access confidential and necessary health information from any hospital, physician, insurer or other reliable source. In the blood bank, blood typing data is obtained rapidly and RF ID labels are appropriately written. The results are automatically compared with those obtained previously during prior admissions or with data from the city blood bank or American Red Cross. Differences, such as new antibodies are noted and the records upgraded throughout. Any obvious clerical or other errors are also ruled out very effectively by this process of comparison the patient deteriorates and undergoes emergency surgery.

Suppose blood is ordered and sent to the operating room (OR). While bringing the blood to the OR, an extra bag that was in storage for another patient is taken unwittingly. When placed in the dedicated patient storage container or area, automatic scanning indicates the presence of this unit of blood. If this should fail a scanner integral to or near the patient ID bracelet would note the discrepancy and issue a warning such that the wrong unit not be given. When each unit is given, the used bags are placed in a waste area, where the RF ID tags are again scanned. This information is sent to the blood bank for closure of the loop. This prevents units from becoming lost or otherwise wasted in a busy OR. This also allows for real time tracking of blood use in the OR by the blood bank, which can then better keep up with demands and improve logistics. This is very important if a nonhospital or city blood center's resources should become required on short notice. Further, the blood bank would avoid unnecessary processing of unneeded blood and blood products which would need to be used quickly or wasted once prepared.

In the foregoing detailed description, devices, systems and methods in accordance with embodiments of the present invention have been described with reference to specific exemplary embodiments. Accordingly, the present specification and figures are to be regarded as illustrative rather than restrictive.

I claim:

1. An assembly of medical products, the assembly comprising:
   a first unit of a medical product including a first unit radio frequency identification (RF ID) device, the first unit RF ID device uniquely identifying the medical product and the first unit;
   a second unit of the medical product having a second unit RF ID device, the second unit RF ID device uniquely identifying the medical product and the second unit;
   a first supplemental RF ID device removably attached to the first unit, the first supplemental RF ID device uniquely identifying the first unit; and
   a second supplemental RF ID device removably attached to the second unit, the second supplemental RF ID device uniquely identifying the second unit.

2. The assembly of claim 1 wherein the RF ID devices are incorporated into labels.

3. The assembly of claim 1 wherein the medical product is a pharmaceutical product.

4. The assembly of claim 1 wherein the medical product is a blood product.

5. The assembly of claim 1 wherein the medical product is a tissue product.

6. The assembly of claim 1 wherein the RF ID devices include source data and unit number data.

7. The assembly of claim 6 wherein the RF ID devices further include drug type data, drug name data, formulation data, interaction data, dosage data, expiration date data, batch number data, indication data, contraindication data or combinations thereof.

8. The assembly of claim 6 wherein the RF ID devices further include blood donor data, blood type data, antigen data, antibody data or combinations thereof.

9. An assembly of medical products, the assembly comprising:
 a first unit of a medical product including a first unit radio frequency identification (RF ID) device, the first unit RF ID device uniquely identifying the medical the product and the first unit;
 a second unit of the medical product having a second unit RF ID device, the second unit RF ID device uniquely identifying the medical product and the second unit; and
 packaging combining the first unit and the second unit into a group, the packaging having a group RF ID device, the group RF ID device uniquely identifying the medical product, the first unit and the second unit.

10. The assembly of claim 9 wherein the medical product is a pharmaceutical product.

11. The assembly of claim 9 wherein the medical product is a blood product.

12. The assembly of claim 9 wherein the medical product is a tissue product.

13. The assembly of claim 9 further including:
 a first supplemental RF ID device removably attached to the first unit, the first supplemental RF ID device uniquely identifying the first unit; and
 a second supplemental RF ID device removably attached to the second unit, the second supplemental RF ID device uniquely identifying the second unit.

14. The assembly of claim 9 wherein the RF ID devices include source data and unit number data.

15. The assembly of claim 14 wherein the RF ID devices further include drug type data, drug name data, formulation data, interaction data, dosage data, expiration date data, batch number data, indication data, contraindication data or combinations thereof.

16. The assembly of claim 14 wherein the RF ID devices further include blood donor data, blood type data, antigen data, antibody data or combinations thereof.

17. The assembly of claim 9 wherein the RF ID devices are incorporated into labels.

18. A method of tracking medical products, comprising:
 associating a group of medical products with a group location based on a group radio frequency identification (RF ID) device signal, the group including a first unit and a second unit;
 associating the first unit with a first remote location based on a first unit RF ID device signal; and
 associating the second unit with a second remote location based on a second unit RF ID device signal, the signals uniquely identifying the units and the group.

19. The method of claim 18 further including:
 receiving the group RF ID device signal, the group RF ID device signal including a group identifier, a first unit identifier and a second unit identifier;
 storing the identifiers to a central database; and
 storing group location data to the central database.

20. The method of claim 19 further including storing product source data to the central database based on the group RF ID device signal.

21. The method of claim 20 further including storing one or more of drug type data, drug name data, formulation data, interaction data, dosage data, expiration date data, batch number data and contraindication data to the central database.

22. The method of claim 20 further including storing one or more of blood donor data, blood type data, expiration date data, antigen data and antibody data to the central database.

23. The method of claim 18 further including:
 receiving the first unit RF ID device signal, the first unit RF ID device signal including a first unit identifier;
 receiving the first unit identifier and first remote location data over a network; and
 storing the first unit identifier and the first remote location data to a central database of a processing system.

24. The method of claim 18 further including:
 receiving the second unit RF ID device signal, the second unit RF ID device signal including a second unit identifier;
 receiving the second unit identifier and second remote location data over a network; and
 storing the second unit identifier and the second remote location data to a central database.

25. The method of claim 18 wherein the medical products includes pharmaceutical products, blood products, tissue products or any combination thereof.

26. A method of tracking medical products, comprising:
 receiving a group RF ID device signal corresponding to a group of medical products located in a receiving area of a health care facility, the group including a first unit and a second unit, the group RF ID device signal including a group identifier, a first unit identifier and a second unit identifier;
 associating the identifiers with the receiving area in a central database;
 receiving a first unit RF ID device signal over a network, the first unit RF ID device signal including a first unit identifier and first remote location data, the first unit RF ID signal indicating that the first unit has moved to the first remote location;
 associating the first unit identifier with the first remote location in the central database in response to receiving a first unit update signal;
 receiving a second unit RF ID device signal over a network, the second unit RF ID device signal including a second unit identifier and second remote location data, the second unit RF ID device signal indicating that the second unit has moved to the second remote location; and
 associating the second unit identifier with the second remote location in the central database in response to receiving a second unit update signal.

27. The method of claim 26 further including:
 storing product source data to the central database based on the group RF ID device signal, the product source data including pharmaceutical manufacturer identification data, blood bank identification data, or any combination thereof; and
 storing patient data to the central database based on the first unit RF ID device signal, the second unit RF ID device signal, or any combination thereof.

* * * * *